(12) United States Patent
Landegren et al.

(10) Patent No.: US 7,790,388 B2
(45) Date of Patent: Sep. 7, 2010

(54) NUCLEIC ACID AMPLIFICATION METHOD

(75) Inventors: Ulf Landegren, Uppsala (SE); Mats Gullberg, Uppsala (SE); Mats Nilsson, Sigtuna (SE)

(73) Assignee: Olink AB, Uppsala (SE)

( * ) Notice: Subject to any disclaimer, the term of this patent is extended or adjusted under 35 U.S.C. 154(b) by 61 days.

(21) Appl. No.: 11/946,706

(22) Filed: Nov. 28, 2007

(65) Prior Publication Data

US 2008/0131899 A1 Jun. 5, 2008

Related U.S. Application Data

(63) Continuation of application No. 10/483,900, filed as application No. PCT/SE02/01378 on Jul. 12, 2002, now Pat. No. 7,320,860.

(30) Foreign Application Priority Data

Aug. 3, 2001 (GB) .................................. 0118959.6

(51) Int. Cl.
*C12Q 1/68* (2006.01)
*C12P 19/34* (2006.01)

(52) U.S. Cl. ......................................... 435/6; 435/91.2

(58) Field of Classification Search ....................... None
See application file for complete search history.

(56) References Cited

U.S. PATENT DOCUMENTS

| 5,854,033 A | 12/1998 | Lizardi |
| 6,221,603 B1 | 4/2001 | Mahtani |
| 6,274,320 B1 * | 8/2001 | Rothberg et al. ................ 435/6 |
| 6,350,580 B1 | 2/2002 | Sorge |
| 6,573,051 B2 | 6/2003 | Alsmadi et al. |
| 6,830,884 B1 | 12/2004 | Hafner et al. |

FOREIGN PATENT DOCUMENTS

| WO | 9201813 A1 | 2/1992 |
| WO | 9700446 A1 | 1/1997 |
| WO | 97/20948 A1 | 6/1997 |
| WO | 9949079 A1 | 9/1999 |
| WO | 00/06778 A1 | 2/2000 |
| WO | 0138580 A2 | 5/2001 |
| WO | 0140516 A | 6/2001 |
| WO | 01/88190 A2 | 11/2001 |
| WO | 2005111236 A1 | 11/2005 |

OTHER PUBLICATIONS

Morris et al., Rapid reverse transcription—PCR detection of hepatitis C virus RNA in serum by using the taqman fluorogenic detection system, Journal of Clinical Microbiology, 34(12)2933-2936 (1996).
Nitsche et al., Different real-time PCR formats compared for the quantitative detection of human cytomegalovirus DNA, Clinical chemistry, American Association for Clinical Chemistry, 45(11)1932-1937 (1999).
Chen et al., A homogeneous ligase-mediated DNA diagnostic test genome research, Cold Spring Harbor Laboratory Press, 8(5)549-556 (1998).
Lizardi et al., Mutation detection and single-molecule counting using isothermal rolling-circle amplification, Nature Genetics, 19(3)225-232 (1998).
Thomas et al., Amplification of padlock probes for DNA diagnostics by cascade rolling circle amplification or the polymerase chain reaction., Arch. Pathol. Lab. Med., 123:1170-1176 (1999).
Chen et al., A homogenous, ligase-mediated DNA diagnostic test, Geneome Res., 8:549-556 (1998).
Ohmichi et al., The virtues of self-binding:high sequence specificity for RNA cleavage by self-processed hammerhead ribozymes., Nucleic Acids Res., 28:776-783 (2000).
Baner, et al, "Signal amplification of padlock probes by rolling circle replication", Nucleic Acids Research (1998), 26 (22):5073-5078.
Carmi, et al, "Cleaving DNA with DNA", Proc. Natl. Acad. Sci. (Mar. 1998), 95: 2233-2237.
Copley, et al, "Exonuclease Cycling Assay: An amplified assay for the detection of specific DNA sequences" BioTechniques, (1992), 13(6):888-892.
Cuenoud et al, "A DNA metalloenzyme with DNA ligase activity", Nature (Jun. 15, 1995), 375: 611-614.
Daubendiek, et al, "Generation of catalytic RNAs by rolling transcription of synthetic DNA nanocircles", Nature Biotechnology, (Mar. 1997), 15: 273-277.
Dauerse, et al, "Multiple colors by fluorescence in situ hybridization using ratio-labelled DNA probes create a molecular karyotype", Human Molecular Genetics, (1992), 1(8):593-598.
Heid, et al, "Real Time Quantitative PCR", Genome Research, (1996), 6:986-994.
Herschlag, et al, "DNA cleavage catalysed by the ribozyme from Tetrahymena", Nature (Mar. 29, 1990), 344: 405-409.
Lizardi, et al, "Mutation detection and single-molecule counting using isothermal rolling-circle amplification", Nature Genetics, (Jul. 19, 1998), 19: 225-232.
Layamichev, et al, "Polymorphism identification and quantitative detection of genomic DNA by invasive cleavage of oligonucleotide probes", Nature Biotechnology, (Mar. 1999), 17: 292-296.
Nederlof, et al, "Fluorescence ratio measurements of double-labeled probes for multiple in situ hybridization bydigital-imaging microscopy", Cytometry, (1992), 13:839-845.
Nilsson, et al, "Padlock probes: Circularization oligonucleotides for localized DNA detection", Science, (Sep. 30, 1994), 265:2085-2088.
Tyagi, et al, "Molecular Beacons: Probes that fluoresce upon Hybridization", Nature Biotechnology, (Mar. 1996), 14:303-308.

* cited by examiner

*Primary Examiner*—Kenneth R. Horlick
*Assistant Examiner*—David C Thomas
(74) *Attorney, Agent, or Firm*—Browdy and Neimark, PLLC

(57) ABSTRACT

A nucleic acid amplification method, and probes for use within the method are described.

22 Claims, 13 Drawing Sheets

NUCLEIC ACID AMPLIFICATION METHOD

The present application is a continuation of application Ser. No. 10/483,900, filed Jul. 20, 2004, which is a national stage under 35 U.S.C. 371 of PCT/SE02/01378, filed Jul. 12, 2002, which claims priority from UK0118959.6, filed Aug. 3, 2001. The entire contents of the prior applications are incorporated by reference.

INTRODUCTION

This invention relates to the generation, amplification, detection and quantification of nucleic acids. More particularly, the present invention relates to the generation, amplification, detection and quantification of circular nucleic acids.

Over the last 20 years nucleic acid amplification has become a common technique in the identification of genetic disorders, genetic variants or for the identification of infectious agents.

Many methods exist for the amplification of nucleic acids. These include the polymerase chain reaction (PCR), and the ligase chain reaction (LCR), both of which require thermal cycling, the transcription based amplification system (TAS), the nucleic acid sequence based amplification (NASBA), the strand displacement amplification (SDA), the invader assay, rolling circle amplification (RCA), and hyper-branched RCA (HRCA).

In the description that follows, the present invention will be described with reference to its preferred use in rolling circle amplification method (Lizardi et al., 1998), U.S. Pat. Nos. 5,854,033, 6,124,120, 6,143,495, 6,183,960, 6,210,884. However, it is not intended to be limited thereto since the invention may find equal utility in other nucleic acid amplification methods, especially other circular amplification methods. The circular nucleic acids referred to in the invention can be circularised probes, circularised target nucleic acids, circular reporter nucleic acids, plasmids, or circular target nucleic acids. The present invention can be used for nucleic acid sequence analyses for e.g. genotyping, finding mutations, sequencing, identification of infectious agents, molecular diagnostics, genetic analyses and forensics, but also for detection of proteins, analysis of protein-protein interactions, and interactions of biomolecules.

The present invention relates to novel means of generating circularized nucleic acids, and to amplify, detect, or analyze the said circularized nucleic acids. Some means of generating circularized nucleic acids for analytical purpose are known in the literature. Padlock probes are oligonucleotide probes that become circularized upon recognition of a target nucleic acid sequence (Nilsson et al., 1994). Proximity probe ligation can template generation of circularized probes as a consequence of target molecule recognition, as described in (Landegren, PCT WO99/49079).

RCA results in a linear amplification of circularized probes and is therefore of limited sensitivity. Typically an RCA produces about 1000 copies of each circularized probe molecule per hour.

It is an object of the present invention to improve the sensitivity of nucleic acid amplification processes, especially RCA processes.

STATEMENTS OF INVENTION

One means of improving the sensitivity of an amplification process, such as for example a RCA process, is to increase the signal obtained during the process. This may be done by performing additional amplification procedures templated by the first generation RCA product. One such additional amplification procedure is obtained by turning the first generation RCA product into a new generation of monomers which themselves are amplified in a further amplification reaction. Accordingly, in a first aspect, the invention relates to a method of amplifying a nucleic acid product, comprising the steps of:

providing a first generation amplification product, typically by RCA, which product comprises a concatemer of a sequence to be amplified;

monomerising the amplification product; and carrying out a further amplification of the thus-formed monomers to form a second generation amplification product.

Preferably, the monomers are ligated to form circles followed by further amplification of the circles, in which case the further amplification is ideally RCA (FIG. 1). The sequence to be amplified may be a probe sequence, or part of probe sequence, or it may comprise cDNA, genomic DNA or RNA sequences.

In one embodiment of the invention, monomerization of the first generation amplification product is achieved using a restriction enzyme and an oligonucleotide complementary to the first generation amplification product, wherein the restriction enzyme cleaves any first generation amplification product/oligonucleotide hybrids. Typically, oligonucleotide is added in excess of the numbers of monomers contained in the first generation reaction product.

Alternatively, the sequence to be amplified may include a catalytically active sequence which enables monomerization of the first generation amplification product (Daubendiek & Kool, 1997).

Typically, the first generation amplification product is produced in a first generation amplification step, which step utilizes a polymerase enzyme, wherein the method includes a step of inactivating the polymerase enzyme. Ideally the polymerization is carried out under isothermal conditions.

When monomerization of the first generation amplification product is achieved using oligonucleotides and restriction enzymes, oligonucleotide is added in excess of the number of monomers present in the RCA reaction product. Most of the oligonucleotides that will hybridise to the monomers after a denaturation (and enzyme inactivation) step will be non-cleaved. Hence, because circularization is favored (at any practical concentrations) over di- or multi-merization due to the intra-molecular nature of this hybridization reaction, the monomers will preferentially become circularized upon hybridization to non-cleaved oligonucleotides and ligase treatment.

This new set of circles is now able to serve as templates for subsequent rounds of RCA, primed e.g. by the same oligonucleotide serving as template for ligation. Therefore, instead of a linear amplification, this procedure will generate a $(X_1 \times X_2 \ldots \times X_n)$-fold amplification, where "X" is the number of monomers synthesized in each RCA, and "n" is the number of rounds of RCAs, digestions and circularizations. The procedure should be of particular value for applications where a large set of different circular nucleic acids is amplified by RCA, since the procedure should preserve the complexity of the initial set of circular nucleic acids. This is due to the intra-molecular nature of the circularization reactions, and because in each round of replication of the circularised nucleic acids is contiguous and processive (one circle->one product carrying thousands of copies of the circle), without interference from any other simultaneously replicating molecule. Furthermore, each round of the reaction should not be product inhibited or primer limited, and does not recruit more polymerases during the polymerization reaction. Hence, the procedure should essentially be independent of the number of different amplified circles. The product of the reaction is single stranded, readily available for detection via hybridisation probes. The linear nature of RCA reactions should ensure faithful quantification quantitative determination of target molecules.

The monomerization can be effected using a general sequence that is present in each of the different probes present in a reaction. In the second generation of the RCA, the risk that the product will become double-stranded (see below) is minimal because all monomers will become circularised, due to the addition of excess cleavage/circularization oligonucleotides. Therefore, there should be no sequences present in the second-generation RCA, and able to prime synthesis on the second-generation RCA product. Also, this polynomial amplification method is completely specific to circularized molecules, reducing the risk for spurious amplification products seen in other amplification methods.

When analyzing gene expression patterns in a highly multiplexed fashion one needs to make an endpoint measurement on for example a microarray. Using the present invention, gene expression can be monitored with high resolution and precision in a multiplexed procedure. Several so called padlock probes, each specific for a gene product or fragment, are circularized by ligation templated by cDNA or RNA. These padlock probes can be encoded by a tag sequence in order to analyze the RCA products on a DNA microarray. An alternative way of amplification is by using PCR. However, PCR is a product inhibited reaction which will reach a plateau-phase after a number of PCR cycles, where after no more products are formed due to reannealing of the DNA strands. This will skew the quantification of abundant transcripts compared to rare ones, since the abundant ones will stop amplifying towards the end of the multiplexed amplification reaction, while rare ones continue to be amplified. The problem of obtaining quantitative endpoint measurements using PCR is well known, and hence the technique of real-time analysis of PCR has been developed where a low number of transcripts (~1-4 transcripts) can be simultaneously analyzed (Heid et al., 1996).

By instead amplifying the circularized padlock probes using the present invention, no such skewing will occur since the reaction is not product inhibited but rather only limited by the substrates, i.e. the deoxynucleotide-triphosphates. This will enable the quantification of very high numbers of transcripts in one single reaction.

The method of replicating a first, second, and maybe more generations of circularized sequences is applicable both for probe and target nucleic acid sequences. The product can be analyzed by sequencing or by detection via e.g. any of the methods described below. In a preferred format for amplification of genomic or cDNA sequences, the target DNA is first fragmented using e.g. restriction enzymes or FLAP endonucleases, and then circularized using a circularization adapter consisting of single-stranded sequences at each end, complementary to the ends of the target DNA fragment to be amplified. It may be advantageous to amplify similar-sized fragments when many different fragments are amplified in the same reaction. It may not be possible to find one restriction enzyme or a combination of restriction enzymes that will generate restriction fragments of a similar size of all sequences in e.g. a genomic DNA sample. But it is very likely that all sequences will be represented on restriction fragments of the desired size in at least one of perhaps ten different restriction digestions using different restriction enzymes or combinations of restriction enzymes. Most advantageously, a double-stranded non-target complementary segment is located in between the single-stranded segments, and that contains a general restriction oligonucleotide sequence (FIG. 2). By using the general restriction oligonucleotide sequence, many different target DNA fragments can be circularized using different circularization adaptors, but can then be amplified using the same general restriction oligonucleotides and enzymes. Similarly to probe circularization reactions, this target circularization reaction is unlikely to give rise to cross-reactive products since the intra-molecular circularization reaction is favored over inter-molecular ligation reactions. Therefore, a multiplicity of different target DNA fragments can be amplified in parallel, unlike amplification methods like PCR. It may be advantageous to amplify similar-sized fragments when many different fragments are amplified in the same reaction. It may not be possible to find one restriction enzyme or a combination of restriction enzymes that will generate restriction fragments of a similar size of all sequences in e.g. a genomic DNA sample. But it is very likely that all sequences will be represented on restriction fragments of the desired size in at least one of perhaps ten different restriction digest using different restriction enzymes or combinations of restriction enzymes. If 1000 different DNA sequences are to be amplified, then they can be amplified in perhaps ten different reactions using DNA samples digested with ten different combinations of restriction enzymes. The appropriate restriction digests and the corresponding circularization adaptors can be deduced from the available sequence databases. Amplified DNA sequences can be analyzed by suitable methods, including but not limited to, microarray hybridization, mini-sequencing, or mass-spectrometry, that today are limited in their through-put due to the limited multiplexing capacity of PCR.

The same mechanism of circularizing monomerized amplification products can be used to generate circularized representations of oligonucleotide probes that have been joined in a proximity-dependent nucleic acid interaction event (Landegren, 1995 and Landegren & Fredriksson, 2000). In this assay binding of two or more probes to a target molecule, e.g. a protein, allows attached DNA strands to be joined by ligation, serving as an amplifiable and detectable indicator of the bound protein. In a preferred embodiment, an excess of restriction oligonucleotide is hybridized to two identical sequences, in two of the joined oligonucleotide probes, containing a restriction enzyme recognition sequence. After restriction digestion and heat-inactivation of the restriction enzyme, cleaved oligonucleotides are detached, allowing an intact restriction oligonucleotide to hybridize to both ends of the joined and digested probe oligonucleotides, due to the preferred intra-molecular hybridization reaction. Upon addition of a DNA ligase, the restriction oligonucleotide acts as a ligation template, guiding the circularization of the oligonucleotide (FIG. 3). The circle that forms can now be amplified according to the present invention. The mechanism of forming circularized DNA as an effect of a proximity-dependent nucleic acid ligation reaction is distinct from the one described in PCT WO99/49079. In the present invention, parts of the proximity probes become circularized, in contrast to the method described in PCT WO99/49079 where proximity probes template circularization of added oligonucleotides.

In one preferred format, circularised amplification products are hybridised to different primers attached to a solid support, specific for each of the different products present in the reaction. The different primers are preferably designed to be as dissimilar as possible, i.e. they represent so-called zip-code- or tag-sequences, and they may be arranged in an array. The primers are used to initiate a localised RCA. By hybridizing the circularized amplification products rather than the initial circular set of nucleic acids, the hybridisation kinetics and sensitivity are improved by several orders of magnitude. Moreover, if a localised RCA is monitored in real-time, a signal accumulation over time could be detected over a very broad dynamic range, particularly suitable for expression analyses. If the complexity of the sample is very high with respect to differences in copy number and/or the number of different sequences, then cross hybridisation between different tag-sequences will be difficult to avoid completely. Therefore, it would be valuable to increase the specificity of zip code recognition, over that attained by oligonucleotide hybridization, by requiring that the solid support attached tag-sequence primers template circularization of the amplified monomers. If the number of different targets is very high, a monomerization procedure must be devised that allows for specific cleavage in each of many different tag-sequences. For this purpose, every sequence in the complex mix of circularizable nucleic acids may be equipped with a type IIs restriction enzyme recognition sequence adjacent to the unique tag-sequence. Specific cleavage within the tag-sequence motif is obtained by rendering the recognition sequence double-stranded with an oligonucleotide having a sequence general for all RCA products and/or a pool of random short oligonucleotides, e.g. hexamers, which will form double-stranded substrates for restriction cleavage (FIG. 4). After restriction digest, the monomers have now in effect been converted to padlock probes containing half-tag end-sequences. Moreover, this strategy allows half-tags connected to pairs of detection reagents to be combined to identify the pairs of binding reagents that have been bound in proximity. This is possible by using proximity ligation probes where ligatable ends constitute unique base-paired half-tag sequences. In this manner ends may be joined by blunt- or sticky end ligation (FIG. 3).

Repeated RCAs has been proposed previously in WO 92/01813 and U.S. Pat. No. 5,714,320. However, in WO 92/01813 the RCA products are cleaved to monomers in order to create new primers for subsequent RCA reactions using preformed circles. In U.S. Pat. No. 5,714,320 a preparative method is described for producing selected oligonucleotides having well-defined ends by providing an isolated circular oligonucleotide template. The method is however not suited for analytical purposes or for amplification of rare circular DNA strands generally, since it typically requires 0.1 µM to 1 mM isolated circular templates. In the method described in U.S. Pat. No. 5,714,320 the primers are provided in a molar excess over circular template of less than 100, and the deoxynucleotidetriphosphates in a molar excess over circular templates of less than $10^7$. For analytical applications these molar ratios are to low to allow efficient priming and polymerization, respectively, due to the low amount of target molecules. For analysis of, e.g. genomic DNA sequences by either amplification of circularized genomic DNA or circularized oligonucleotide probes, the corresponding molar ratios required in the first amplification step are at least 100 and $10^7$, respectively, or more preferably greater than 100 000 and $10^{10}$, respectively, or ideally about, $10^7$ and $10^{12}$, respectively, because of the low concentration of initial circularized nucleic acids. Japanese patent application JP 4-304900 describes the use of RCA for detecting circularised probes. In this application repeated RCAs are described using the RCA product as a target for subsequent probe ligations and RCAs. By contrast, in the present invention the monomerised RCA product is used as probe in subsequent ligations and RCAs. The advantages of this procedure have already been discussed.

In a further aspect of the invention, the present inventors have devised several approaches for increasing the signal obtained from an RCA by adding a linear signal-generating amplification of the RCA product. This results in an amplification of the signal from circularized probes that grows as a square function of time.

The first approach is based on selective, hybridisation-dependent, degradation of a probe complementary to the RCA product. It is desirable that the probe is designed in a manner such that its cleavage is detectable. Accordingly, in a further aspect, the invention comprises a method of nucleic acid amplification that employs probes to indicate the extent of the amplification, which method comprises the steps of:

providing a signaling probe, which probe includes a sequence which is complementary to an amplification product;

reacting the signaling probe with the amplification product;

selectively degrading signaling probes that have hybridized to the first generation amplification product, wherein degraded probes dissociate from the first generation amplification product allowing further signaling probes to hybridize with the product, wherein hybridization and degradation of the probes effects a change in detection signal emitted by the probe.

Preferably, the probe consists of a hairpin-loop probe, a so-called molecular beacon (Tyagi & Kramer, 1996) comprising a detectable marker ligand therein, which selectively emits a detectable signal. The marker may be part of the nucleic acid sequence or may be a ligand held within the hairpin formation. Preferably, the ligand is released from the nucleic acid on cleavage of the nucleic acid.

If the part of the probe hybridising to the RCA product at least partially consists of RNA it will, upon hybridisation, be degrade by the enzyme RNase H. (Duck et al, e.g. U.S. Pat. Nos. 5,011,769, 5,660,988, 5,403,711 and 6,121,001)

A similar effect can be obtained by substituting one or more of the deoxynucleotides, used in the RCA, for thiophosphorodeoxynucleotides, thereby protecting the RCA product from endonuclease hydrolysis. The molecular beacon would in this case be made of ordinary deoxynucleotides and would therefore be susceptible to degradation by a double strand specific endonuclease. Specifically, a restriction enzyme recognition site can be designed into the loop sequence of the beacon. There are several known restriction enzymes that specifically cleave the non-thiophosphorylated strand when this is hybridised to a thiophosphorylated strand. By analogy to the RNaseH degradable probe, this would only result in cleavage and thereby signal emission from of the probe in the presence of the target molecules. Instead of a specific endonuclease, any unspecific double strand specific endonuclease can be used, thereby avoiding the need for a specific sequence in the probe.

A related way of producing detectable cleavage products is to add a probe complementary to an RCA product and a restriction enzyme that recognise a sequence in the RCA-oligonucleotide duplex. After cleavage of the RCA-oligonucleotide duplex, the cleaved probe will dissociate from the monomerized RCA products. Then an intact oligonucleotide can hybridise to one end of the cleaved monomer, whereafter the other end of the monomer will most likely hybridise to the same oligonucleotide, due to the intra-molecular nature of the interaction. In this manner, a new substrate for the restriction enzyme is formed, and a second signal-generating cleavage occurs. By labelling the probe with a fluorescent moiety at one end and a quencher molecule at the other end a signal will be generated upon cleavage and subsequent dissociation.

Hybridisation-dependent degradation of probes can also be performed with any double strand-specific exonuclease ((Copley & Boot, 1992), U.S. Pat. No. 6,121,001). In this case a probe that hybridise to the RCA product will be a substrate for the exonuclease and thereby degraded while the RCA product are unaffected due to the lack of any double stranded ends. Upon degradation the melting temperature of the duplex will decrease and the probe is more likely to dissociate even if not fully degraded. Thereby the sequence is made accessibly for another probe to hybridise and subsequently be degraded.

This approach for increasing the signal can also be performed with ribo- or so called DNA-zymes (R/D-zyme) (e.g. (Herschlag & Cech, 1990) & (Carmi et al., 1998). By incorporating the complementary sequence of an R/D-zyme in the circularised nucleic acid the RCA product will contain the active R/D-zyme. This can then be used to cleave a probe that is added to the reaction mixture. Upon cleavage the cleaved probe will dissociated from the RCA product and leave place for another uncleaved probe to hybridise and be cleaved. The R/D-zyme does not need to cleave the probe but it can instead template ligation of two oligonucleotides together and generate a signal as described below (Cuenoud & Szostak, 1995).

Probes may also be designed so that upon hybridisation to the RCA product they assemble in such a way that they resemble the substrate for a structure specific enzyme. The enzyme is preferably selected from the group comprising resolvases, recombinases or nucleases, examples Ruv ABC, Holliday junction resolvases, Flip recombinases, FEN nuclease or certain polymerases. One aspect of the invention is to use two oligonucleotides hybridising in tandem in such a way that the downstream oligonucleotide has a protruding 5 prime end. This structure can be cleaved by several different enzymes e.g. FEN nucleases, Taq polymerase, Tth polymerase or Mja nuclease (Lyamichev et al, 1999). The downstream oligonucleotide is designed so that it has a melting temperature near the temperature of the isothermal RCA reaction.

Accordingly, the probes may comprise a fluorescent moiety and a quenching moiety which are separated by a hairpin-loop structure, wherein the quenching moiety quenches the signal from the fluorescent moiety when the probe is in an un-bound and intact conformation the quenching moiety quenches the signal from the fluorescent moiety, and wherein bound or degraged probe emits a signal (FIG. 5). Alternatively, the probe may include a pair of signalling moieties, which moieties produce a signal by FRET when the probe is intact, but where degradation of the probe inhibits signal production.

Advantageously, with the above combination of a probe with any of the hybridization-dependent accumulation of detectable moieties the reaction can continue isothermally, even at low temperature.

In this manner the temperature may be less than 60° C. and preferably is less than 50° C. Advantageously, this may remove the need to maintain the reactions at an elevated temperature.

Instead of degrading probes it is possible to assemble probes to mark the presence of an RCA product. If two oligonucleotide probes are constructed in such a way that they hybridise adjacent to each other on the RCA product, then they can subsequently be joined by a ligase. If the two oligonucleotides are designed in such a way that upon ligation and dissociation from the target they form a stable stem-loop structure, a donator molecule at the 5 prime position can be placed in close proximity to a acceptor molecule at the 3 prime position in the other oligonucleotide. A signal can then be generated based upon fluorescence resonance energy transfer (FRET). By designing the probes so that the ligated probe will have a melting temperature near the temperature of the isothermally proceeding RCA reaction a fast turnover will be possible. The unligated probes will be present in large molar excess over the produced ligated probes, thereby increasing the rate at which they will hybridise to the target RCA product and subsequently be ligated, dissociate and so on. The reaction is thus possible to perform isothermally.

Accordingly, in a further aspect, there is provided a method of nucleic acid amplification which employs probes to indicate the extent of the amplification, which method employs a pair of signaling probes, which probes are designed such that they hybridize to a target sequence on an amplification product adjacent to each other, wherein upon hybridization the probes are ligated to form a ligated product which dissociates from the target sequence, wherein dissociation of the ligated product from the target sequence allows a further pair of probes to hybridize to the target sequence, and wherein upon dissociation from the target sequence the ligated product emits a signal.

Preferably, one of the pair of signaling probes comprises a donor moiety and another comprises an acceptor moiety, and wherein the probes are designed such that the ligated product forms a hairpin loop structure, which upon formation allows energy transfer between the donor and acceptor moieties to produce a signal.

In yet another aspect, the invention comprises homogenous detection of concatemer amplification products using a modified molecular beacon design. The present inventors have found that conventional molecular beacons generate signal in the absence of an RCA product but in the presence of DNA polymerase, unless at least parts of the DNA residues in the beacon are replaced by nucleic acid residues that are not accepted as substrates for the polymerase, since the 3' end (usually carrying the fluorescence quencher) is degraded by the 3' exonucleolytic (proof reading) activity of the polymerase. Generation of non-specific signal can be completely avoided by using molecular beacons comprising 2'-O-methyl-RNA residues instead of DNA residues (FIG. 6). The inventors further found that conventional molecular beacons that hybridise to an RCA product are quenched, because neighbouring beacons readily form stems with each other (inter-molecular stems), bringing the quencher and reporter fluorophores close together, much like the closed (quenched) conformation of non-hybridising beacons (FIG. 7). This can be avoided by including one of the stem sequences of the beacon in the padlock probe sequence so that, upon hybridisation to the RCA product, one part of the stem hybridises to the product so that it cannot form stem-like structures with neighbouring beacons (FIG. 7). With these modifications the RCA can be monitored in real-time (FIG. 8). Alternatively, a second probe could be added to the detection reaction that hybridises to the RCA product in between the molecular beacons to avoid that this sequence loops out, thus hindering the inter-molecular stems to form. The magnitude of the inter-molecular quenching may vary between different molecular beacon sequences as exemplified by the complete quenching of the DNA molecular beacon version (FIG. 9) compared to the partial quenching of the 2'-O-Me-RNA beacon used in FIG. 8.

The inter-molecular hairpin structure that forms between adjacent molecular beacons, hybridising to a concatenate sequence, can also be used to generate FRET between two molecular beacons that hybridise within one monomer of the concatenate sequence. The two molecular beacons should be equipped with the same stem sequence, but the position of the donor and acceptor fluorophores should be switched in one of the two molecular beacons. Such molecular beacons will hybridise in an alternating fashion, forming inter-molecular hairpin structures between adjacent, but alternating molecular beacons, such that the fluorophore of one beacon is positioned in close proximity to the fluorophore of the neighbouring molecular beacon, enabling efficient FRET between the two fluorophores. In this way background fluorescence from closed molecular beacons can be diminished, increasing detection sensitivity.

In a yet further aspect, the invention comprises homogenous detection of concatemer amplification products by virtue of the increased concentration of signaling probes hybridized to the amplification product, compared to the concentration of non-bound signaling probes free in the surrounding solution. The homogenous detection is possible because the long concatemer amplification products are coiled when free in solution and form micrometer-sized balls. The enrichment of signaling probes in the balls of DNA allows convenient detection of single amplification products from individual circularized probes in microscopic analysis, due to the contrast between the condensed signal from the signaling probes hybridizing to the product and the relatively diffuse, fainter signal from non-bound probes (FIG. 12). When for example analyzing gene expression, the number of RCA product balls will directly correspond to the gene expression level. Such a homogenous detection system is very convenient and accurate, since each counted RCA-product corresponds to one detected transcript molecule.

Multiplexed homogenous analyses are generally limited by the number of fluorophores which can be spectrally resolved. If several fluorescently labeled probes are added to for example a PCR reaction, overlapping spectra become a major problem, since the sum of the different fluorophores in the reaction is analyzed. However, in the present invention the analysis of individual RCA products by fluorescence labeled probes can be performed in high multiplex, because fluorophores with closely resembling spectra can be resolved since individual RCA product balls are analyzed, hence no spectral cross-talk.

The homogenous detection can be multiplexed for gene expression analysis or for multiplexed genotyping, by including different zip-code sequences in the different amplified probes, to allow identification of the amplification products by hybridizing ratio-labeled zip-code oligonucleotides to different amplification products. Ratio-labeling is well known in the art and has been used to create multiple color-blends from a limited number of primary colors (Dauwerse et al., 1992, and Nederlof et al., 1992). For example, if two primary dyes A and B are mixed as follows: 0% A and 100% B, 20% A and 80% B, 40% A and 60%, 60% A and 40% B, 80% A and 20% B, and 100% A and 0% B, six different color-blends are created. If three primary dyes are mixed with a similar increment, 36 color-blends can be distinguished. The zip-code oligonucleotides are easily ratio-labeled by either mixing different proportions of fluorescent dye and conjugating these mixes with different zip-code oligonucleotides, or mixing zip-code oligonucleotides labeled with different dyes in the desired proportions. The degree of multiplicity in this labeling approach depends on the number of primary dyes added to the labeling scheme (n), and the precision of the labeling determining the number of ratio increments (x), which limits the number of color blends that can be distinguished $x^{(n-1)}$. Since the amplification products can consist of thousands of repeated units, the precision in the ratio-labeling should be very high, and the contribution of any minor cross-hybridizing zip-code oligonucleotides would be negligible. The major advantages of using the ratio-labeling approach compared to the combinatorial labeling approach, which uses binary (all-or-none) combinations of primary dyes to create multiple pseudo-colors, is that many more color-blends can be obtained using color-ratios compared to color-combinations.

In some embodiments of the present invention it may be advantageous to eliminate any linear probes before the initial RCA, e.g., it has been noticed that remaining non-circularised probes produce a non-specific signal in RCAs. An attempt to overcome this problem is described in WO 00/36141 where enzymes or so-called capture ligands are used to remove any remaining linear nucleic acid probes.

Accordingly, in a further aspect, the present invention relates to a method of removing or rendering inert non-circularized probes during (or after) a nucleic acid amplification process which utilizes circular probes, in which the non-circularized probes comprise first and second segments separated by a linking segment, wherein the first and second segments are complementary to sequences on a target sequence, wherein the probe is designed to form a hairpin loop structure between the 3' end of the probe and a sequence in a linking segment of the probe, wherein a stem of the hairpin loop structure ideally has a thermal stability that neither inhibits formation of a hybrid between the loop and the target sequence nor inhibit replication of the probe by RCA.

The stem should be sufficiently stable to prime synthesis and thus convert non-ligated probes to full hairpins, unable to prime "second strand" synthesis on the RCA-product.

Additionally, the hairpin-forming probe has a further advantage in that such a probe design may be more specific than conventionally designed probes. In conventional probe design the diagnostic base should be positioned at the ultimate 3' position of the probe sequence to fully take advantage of the mismatch discriminatory capacity of DNA ligases. In the hairpin probes of the present invention, this diagnostic base will thus be a part of the hairpin forming sequence. This sequence may be designed to flip back and forth between the hairpin and the target hybridising conformation at the ligation temperature. The matched sequence version of a probe will then spend more time in the target sequence hybridising conformation than the corresponding mismatched probe version. This will favour ligation of matched probes over misligation of mismatched probes.

In a further aspect, the invention provides a further method of removing or rendering inert non-circularized probes during (or after) a nucleic acid amplification process which utilizes circular probes, in which an excess of oligonucleotides that are complementary to a 3' end of the probes are added before the amplification reaction, which oligonucleotides preferably include a 5' sequence extension, whereby the 3' end of non-circularized probes will lose complementarity to a product of the amplification process Preferably, the excess of oligonucleotides which are complementary to the 3' end of the probes are added to the system before the RCA is begun although they may be added simultaneously with the other reagents or immediately after the reaction is begun.

According to the invention, the 3' ends of non-ligated probes will lose their complementarity to the RCA product, and will not be able to prime a second strand synthesis. These 3' eliminators may be used to prime the RCA.

Alternatively, to avoid the situation where the linking segment of non-ligated probes becomes replicated, the 3' eliminators may be equipped with an unextendable 3' end that is also unremovable by 3' exonucleolytic activities of DNA polymerases. This may be particularly important if the RCA product is intended to be detected by oligonucleotides recognizing sequences in the RCA product that correspond to the linking segment of the padlock probes. In this case a general primer could be added to the circularised probes to initiate the RCA. Because of the limited length of the 3' eliminators, they will become displaced by the polymerase extending the primer and will thus not inhibit the RCA (Banér et al., 1998).

DETAILED DESCRIPTION OF THE INVENTION

Embodiments of the invention will now be described in more detail, by way of example only, with reference to the accompanying drawings of which:

FIG. 1 illustrates the general procedure of several generation rolling circle replication (RCA) according to the invention, 1) a padlock probe is hybridized to a specific target nucleic acid strand, 2) the padlock probe is circularized using a DNA ligase, 3) the circularized probe is replicated in an RCA, 4) an excess of oligonucleotides are hybridized to a restriction enzyme recognition sequence present once per monomer of the RCA product, 5) the RCA product is monomerized using a restriction enzyme that digests the oligonucleotide/product duplexes, 6) after a heating step that inactivates the restriction enzyme and denature the oligonucleotide fragments, an absolute majority of the monomers will hybridize with both ends to intact oligo-nucleotides, 7) the monomers are circularized using a DNA ligase and the thus formed circles can now be treated according to steps 3-7 for additional cycles;

FIG. 2 illustrates the amplification of genomic- or cDNA fragments using a circularization adaptor to circularize and amplify the sequences according to the invention, 1) a DNA sample is fragmented using e.g. a restriction enzyme, 2) the fragmented DNA is denatured, 3) a circularization adaptor is hybridized to a specific target fragment, 4) the target fragment is circularized using a DNA ligase, 5) the circularized target fragment is replicated in an RCA, 6) an excess of a general adaptor oligonucleotide is hybridized to a restriction enzyme recognition sequence present in the adaptor sequence once per monomer of the RCA product, 7) the RCA product is monomerized using a restriction enzyme that digests the oligonucleotide/product duplexes, 8) after a heating step that inactivates the restriction enzyme and denature the oligonucleotide fragments, an absolute majority of the monomers will hybridize with both ends to intact oligonucleotides, 9) the monomers are circularized using a DNA ligase and the thus formed circles can now be treated according to steps 5-9 for additional cycles;

FIG. 3 illustrates the conversion of a proximity-dependent ligation event to circularized DNA that can be amplified according to the present invention, 1) a pair of proximity probes, e.g. antibodies equipped with oligonucleotides, binds to a target protein, 2) the two oligonucleotide are joined in a proximity-dependent ligation reaction, e.g. via blunt end ligation to allow half-tag ligation for the identification of pairs of binding reagents that have been bound in proximity, 3) an excess of oligonucleotides are hybridized to two identical sequences containing a restriction enzyme recognition sequence and present in both of the joined oligonucleotide sequences, 5) the joined product is cleaved using a restriction enzyme that digests the oligonucleotide/product duplexes, 6) after a heating step that inactivates the restriction enzyme and denature the oligonucleotide fragments, an absolute majority of the cleaved ligation products will hybridize with both ends to intact oligonucleotides, 7) the monomers are circularized using a DNA ligase and the thus formed circles can now be treated according to steps 3-7 in FIG. 1;

FIG. 4 illustrates how a complex set of RCA products can be monomerized in the middle of a zip-code motif using a type IIs restriction enzyme and random hexamers, and how the monomerized RCA products then are hybridized and circularized on a zip-code oligonucleotide microarray for increased specificity and dynamic range, 1) a set of RCA products containing identifying zip-code oligonucleotide sequences has been generated from e.g. multiplexed padlock probe genotyping or expression analysis experiments, or a multiplexed proximity-dependent ligation event, 2) a type IIs restriction enzyme is added along with a set of random hexamers and a general oligonucleotide containing a type IIs is restriction enzyme recognition sequence, 3) the hexamers and the restriction oligonucleotides are optionally removed and the monomers have now in effect been converted to padlock probes with half zip-code end-sequences, 4) the monomers are hybridized to zip-code oligonucleotide microarray, 5) the monomers are circularized on the zip-code oligonucleotides using a DNA ligase, 6) the monomers are amplified in a RCA using the zip-code oligonucleotides as primers, and the polymerization may optionally be monitored in a homogenous format for increased dynamic range;

FIG. 5 is a schematic representation of the amplification method of the invention whereby molecular beacons are degraded;

FIG. 6 is a graph showing removal of non-specific accumulation of fluorescence in presence of DNA polymerase by replacing all DNA residues of the molecular beacon with 2'O-Me-RNA residues where one DNA molecular beacon is labeled with FAM fluorescence (upper panel) and one 2'O-Me-RNA molecular beacon is labelled with HEX fluorophore (lower panel) which was added to the same test tube in presence (squares) or in absence (circles) of Φ29 DNA polymerase;

Figure 11:
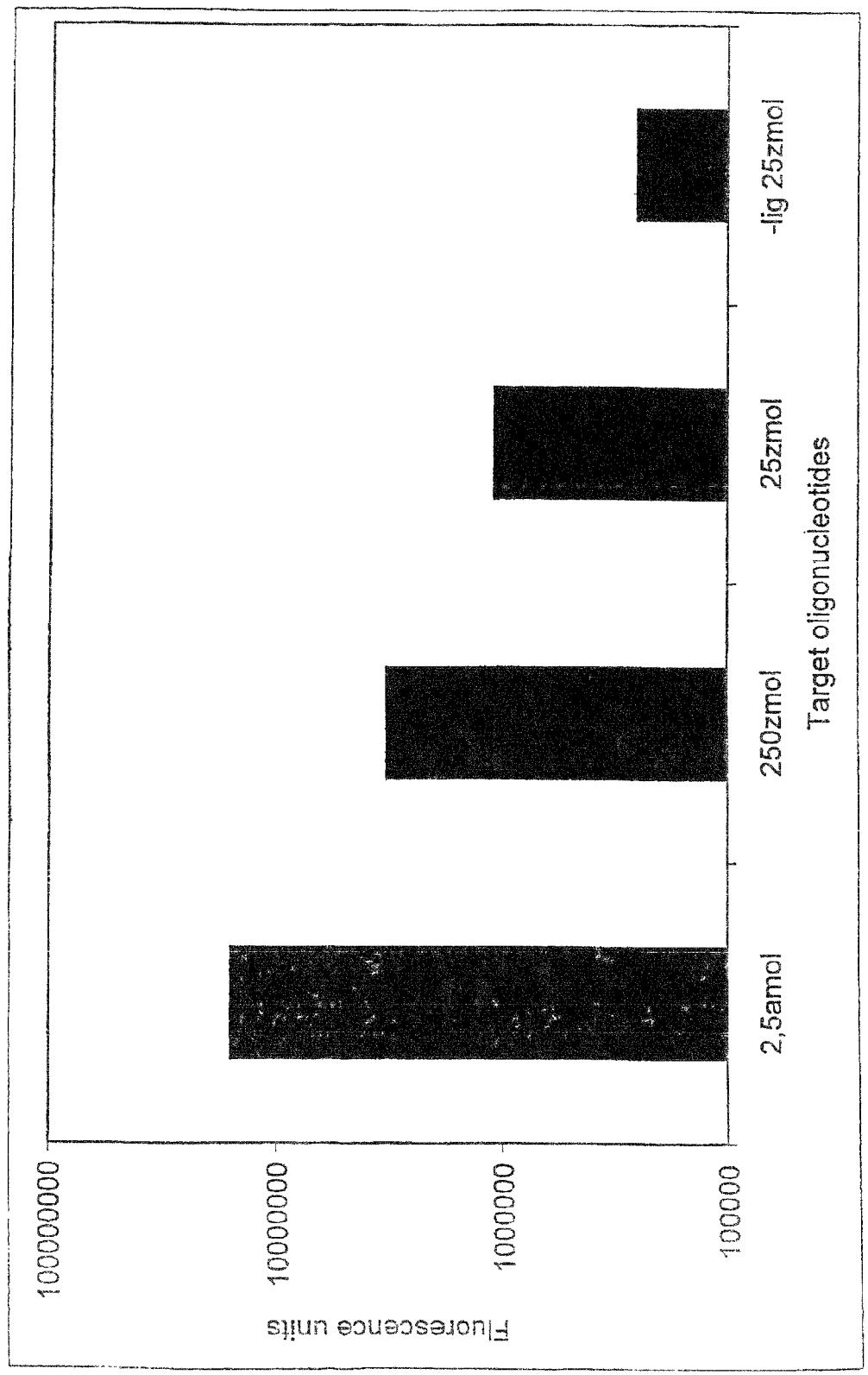
Figure 12:

FIG. 11 shows the fluorescence recorded at a microarray feature containing an oligonucleotide complementary to the second-generation RCA product obtained according to example 2; and FIG. 12 shows individual RCA products in solution detected by homogenous hybridization of fluorescence labeled oligonucleotides, demonstrating the contrast between the condensed signal from the fluorescence labeled oligonucleotides hybridizing to the product and the relatively diffuse, fainter signal from non-bound oligonucleotides.

EXAMPLES

Example 1

Real-Time Monitoring of a Third-Generation RCA Using Modified Molecular Beacons 2 nM padlock probe (P-CCTCCCATCATATTAAAG-GCTTTCTCTAT GTTAA GTGACCTACGACCTCAAT-GCTGCTGCTGTACTACTCTTCCTA AGGCATTCTG-CAAACAT; SEQ ID NO:1) (P=5' phosphate) was circularized in 10 mM TrisAc (pH 7.5), 10 mM MgAc$_2$, 50 mM KAc, 0.1% BSA, 1 mM ATP, 200 mM NaCl, and 20 mU/μl T4 DNA ligase in presence of 0, 10, 40, or 160 zmol of a target oligonucleotide (GCCTTTAATATGGGAGGAT-GTTTGCAGAATGCCTTAG; SEQ ID NO:2). The reactions were incubated for 15 minutes at 37° C., and then the ligase was inactivated for 5 minutes at 65° C. The first-generation RCA was performed for 45 minutes at 37° C. in 0.1 μg/μl BSA, 250 μM dNTP, 10 mM DTT, 1 pmol primer (CGTCG-TAGGTCACTTAACAT; SEQ ID NO:3), and 1 ng/μl φ29 DNA polymerase. The polymerization components were added to 10 μl ligation reactions in 15 μl of φ29 DNA polymerase buffer (10 mM Tris-HCl (pH 7.5), 10 mM MgCl$_2$, and 20 mM (NH$_4$)$_2$SO$_4$ The DNA polymerase was inactivated for 10 min a 65° C. The first-generation RCA product was monomerized by adding 5 μl 0.1 μg/μl BSA, 3 pmol RSAI (GCT-GCTGTACTACTCTCTT; SEQ ID NO:4), and 10 U RsaI in φ29 DNA polymerase buffer. The reaction was incubated for 60 minutes at 37° C. and then the enzyme was inactivated for 10 minutes at 65° C. The monomerized RCA product was circularized by adding 5 μl 0.1 μg/μl BSA, 1 mM ATP, and 1 U T4 DNA ligase in φ29 polymerase buffer. The ligation was incubated for 15 min at 37° C. and then the enzyme was inactivated for 5 minutes at 65° C. The second-generation RCA was performed using the same conditions as the first-generation RCA by adding 15 μl polymerization reagents to 35 μl of the circularized RCA product. The polymerization reaction continued for 45 minutes at 37° C. Half of the second-generation RCA product was monomerized by adding 6 pmol RSAI comp (AAGAGAGTAGTACAGCAGC; SEQ ID NO:5) and 10 U RsaI in 5 μl φ29 DNA polymerase buffer including 0.1 μg/μl BSA. The reaction was incubated for 60 minutes at 37° C., and then the enzyme was inactivated for 10 minutes at 65° C. Circularization of the monomerized second-generation RCA product was performed using the same procedure as the circularization of the monomerized first-generation RCA product. The third-generation RCA was performed as the second-generation RCA but in presence of 0.1 μM molecular beacon (HEX-ccucAAUGCUGCUGCU-GUACUACgagg-DABCYL; SEQ ID NO:6) and for 60 min. The reaction was followed in real-time using an ABI 7700.

Example 2

Detection of a Second-generation RCA Product on a DNA Microarray 2 nM padlock probe (WD 1216G) was circularized as above in presence of various amounts of target oligonucleotides (T 1216G; 0, 25, 250, or 2500 zmol). The first-generation RCA was performed for 100 minutes at 37° C. as above 1 pmol of the primer WDP-F. The polymerization components were added to 10 μl ligation reactions in 15 μl of φ29 DNA polymerase buffer The DNA polymerase was inactivated for 10 min at 65° C. The first-generation RCA product was monomerized by adding 5 μl 0.1 μg/μl BSA, 3 pmol Comp WDP-F, and 5 U Fnu4H 1 in φ29 DNA polymerase buffer. The reaction was incubated for 60 minutes at 37° C. and then the enzyme was inactivated for 10 minutes at 65° C. The monomerized RCA product was circularized by adding 5 μl 0.1 μg/μl BSA, 1 mM ATP, and 1 U T4 DNA ligase in φ29 polymerase buffer. The ligation was incubated for 15 min at 37° C. and then the enzyme was inactivated for 5 minutes at 65° C. The second-generation RCA was performed using the same conditions as the first-generation RCA by adding 15 μl polymerization reagents to 35 μl of the circularized RCA product. The polymerization reaction continued for 100 minutes at 37° C. Half of the second-generation RCA product was monomerized by adding 4.5 μmol D-RCRcut and 5 U Fnu4HI in 5 μl φ29 DNA polymerase buffer including 0.1 μg/μl BSA. The reaction was incubated for 60 minutes at 37° C., and then the enzyme was inactivated for 10 minutes at 65° C. 30 μl 1 monomerized second-generation RCA product was hybridized to a DNA microarray in 4*SSC, 0.525 μM Comp WD Cy5, 10 μM EDTA at 45° C. for 2 h, washed in 0.1×SSC at 45° C., rinsed in water, and finally dried. The Cy5 fluorescence signal was recorded in a fluorescence laser scanner.

Figure 1:
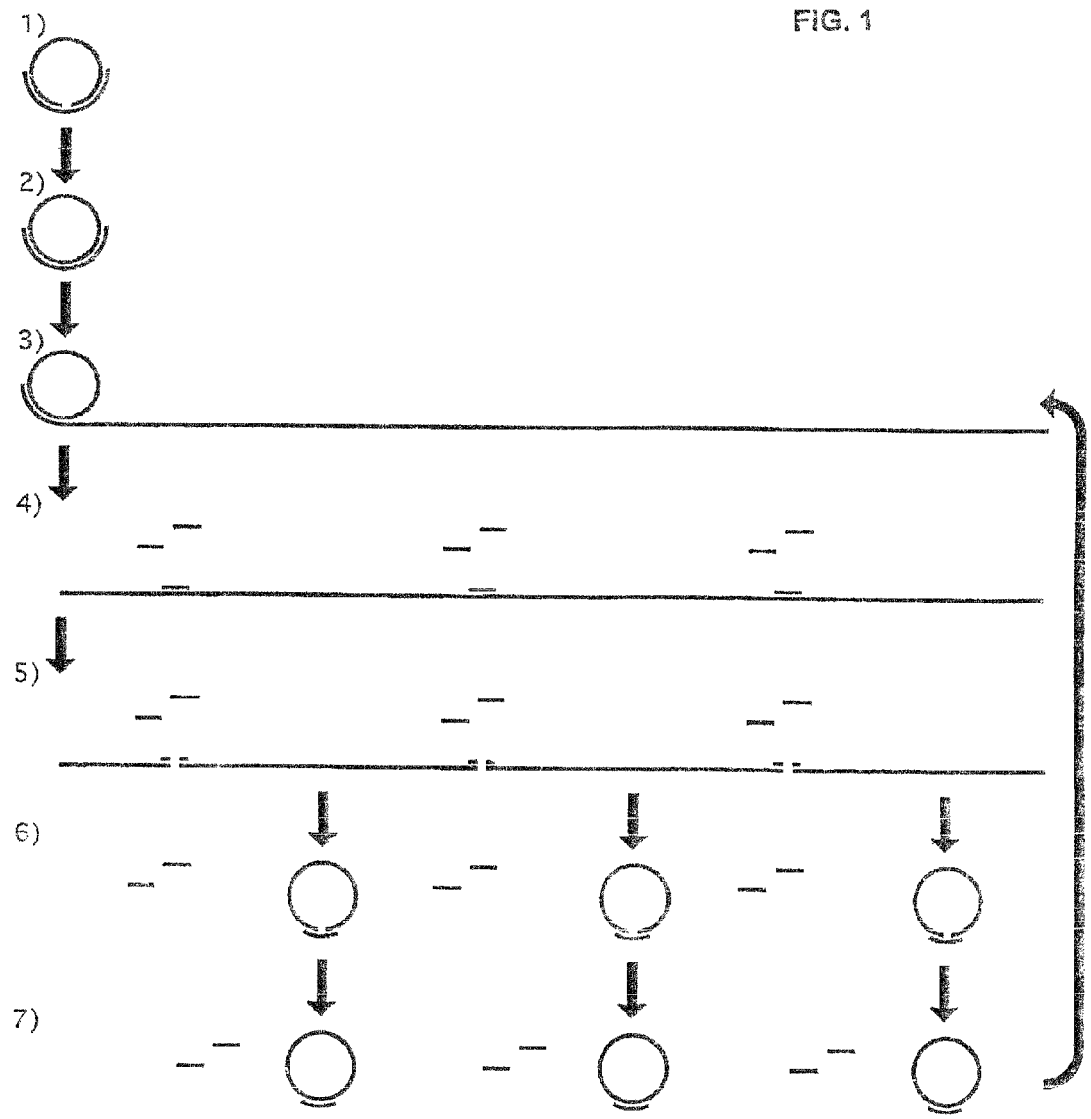
Figure 2:
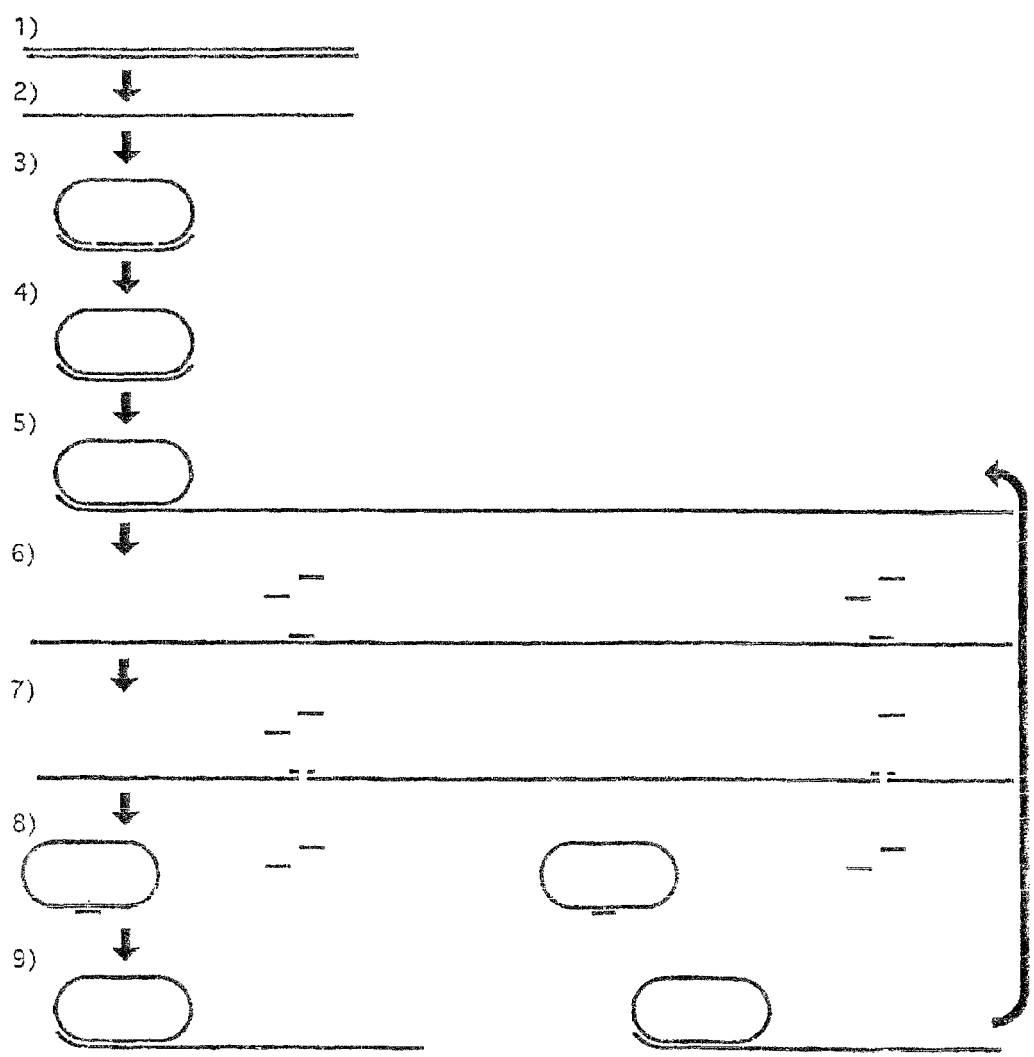
Figure 3:
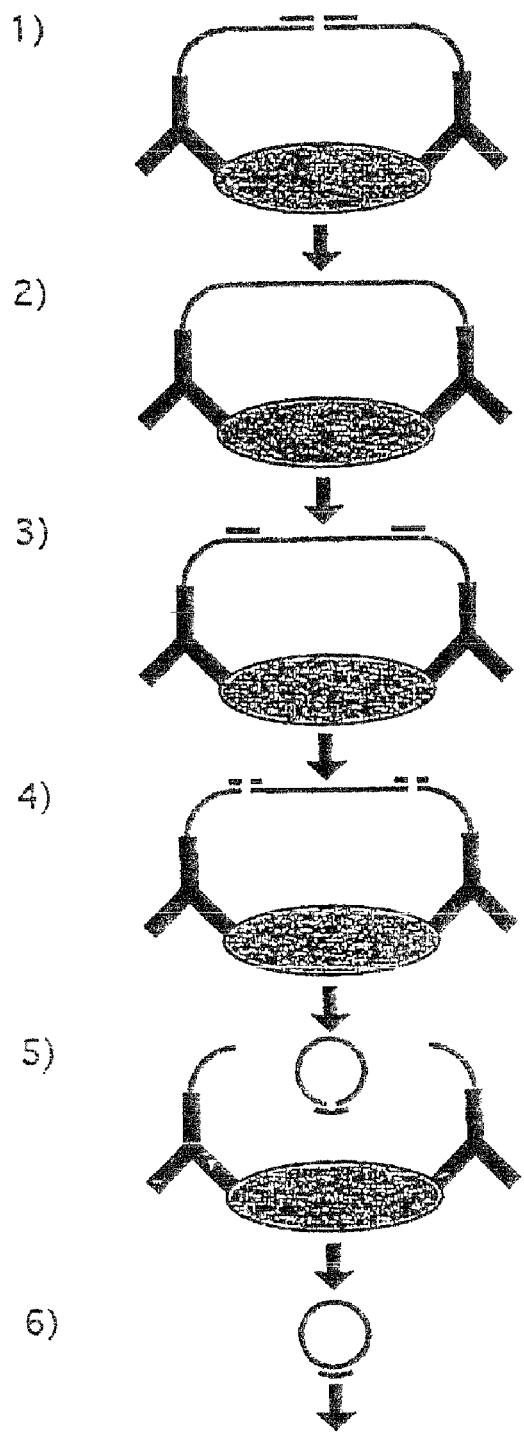
Figure 4:
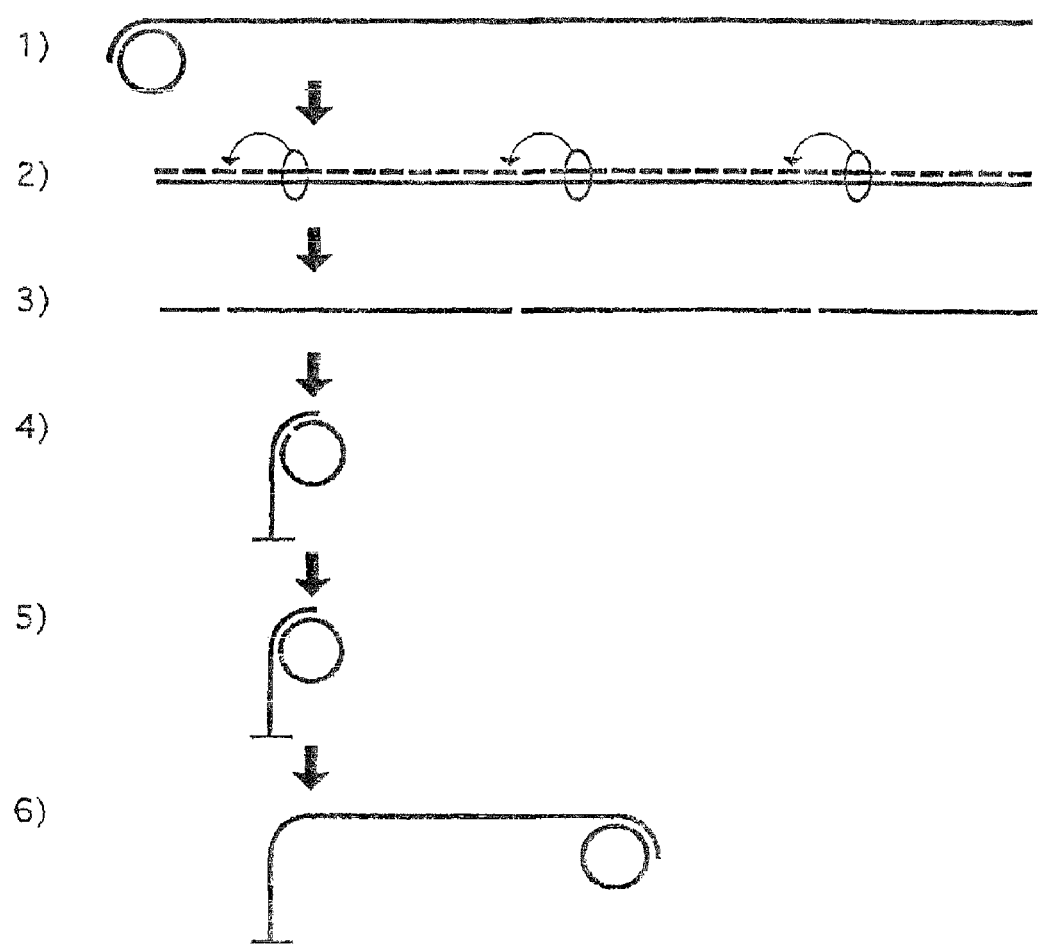
Figure 5:
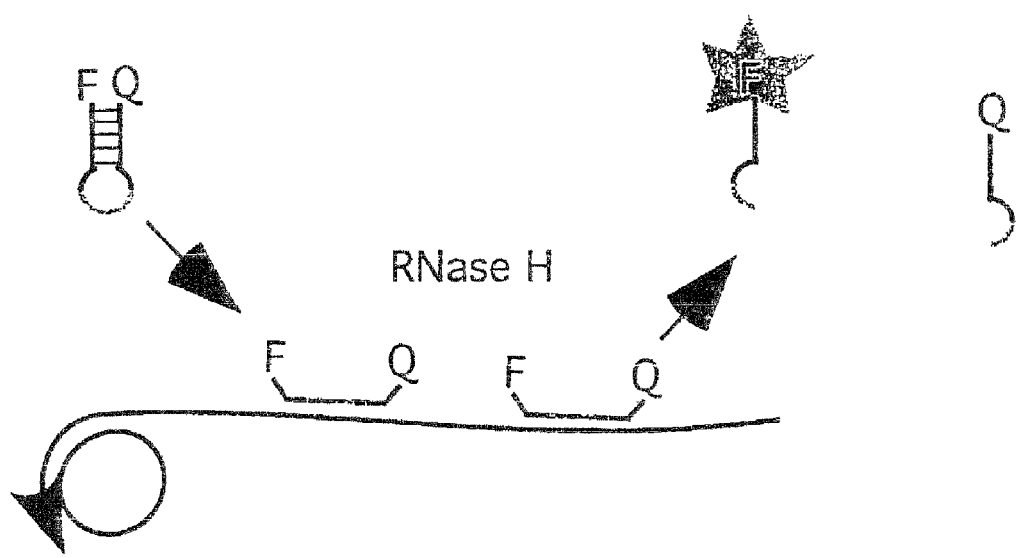
Figure 10A:
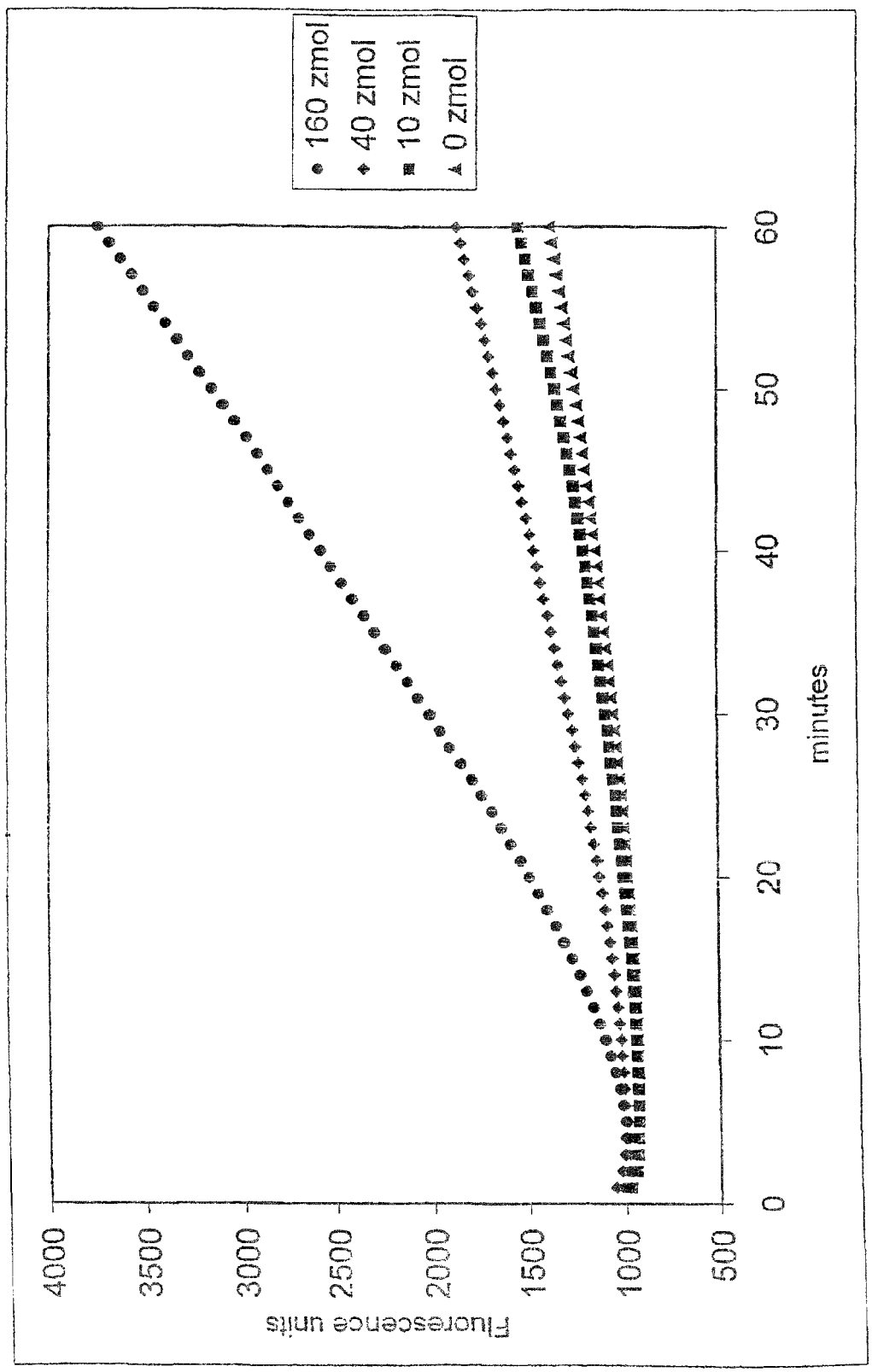
FIG. 10 shows real time monitoring of third generation RCA according to example 1.
Figure 10B:
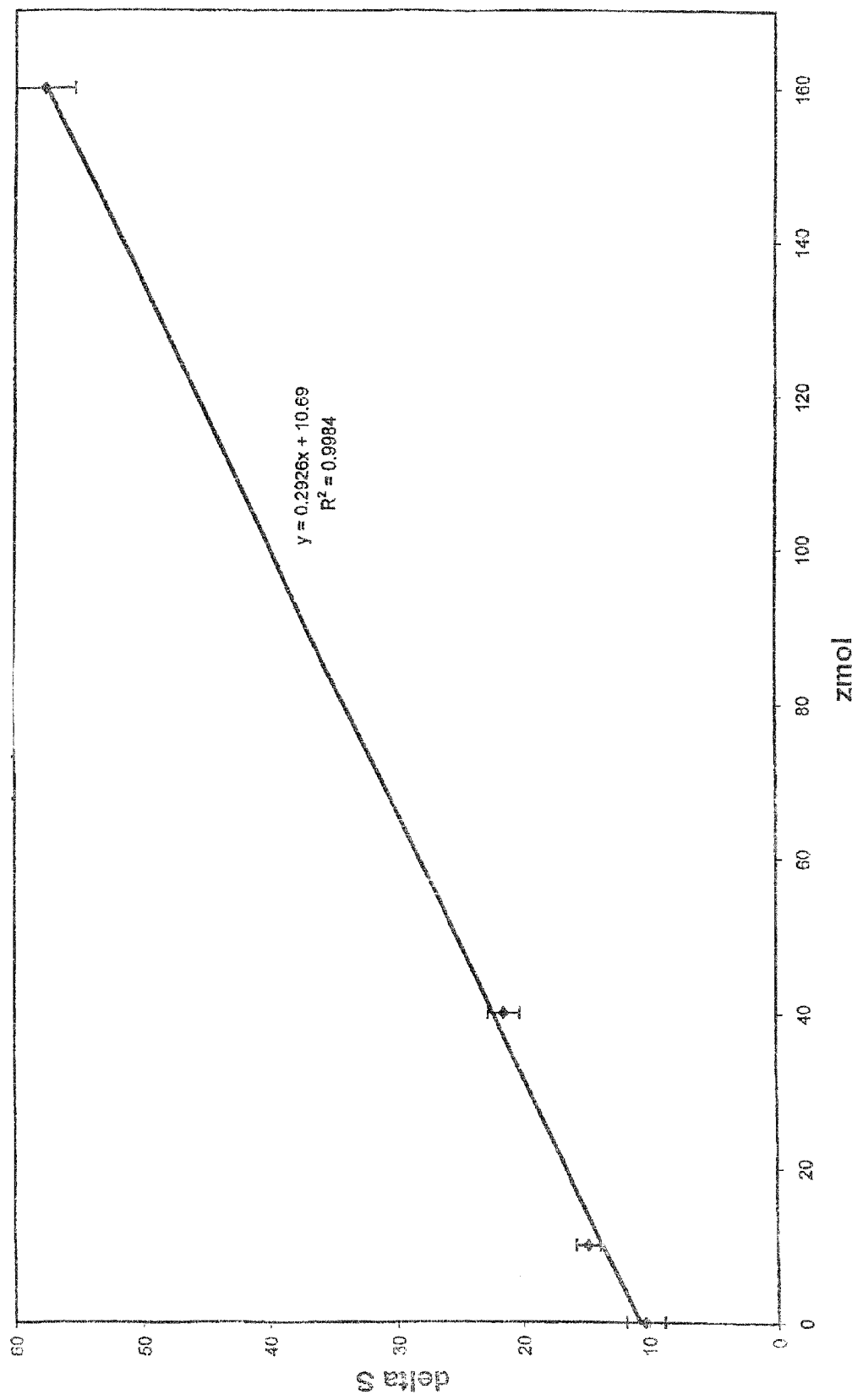

A schematic drawing of the general procedure of a several generation RCA, as described in examples 1 and 2 is illustrated in FIG. 1. The results of examples 1 and 2 are shown in FIGS. 10 and 11, respectively. First a circular nucleic acid is replicated in an RCA. Then the first-generation RCA product is monomerized, e.g. by using a restriction enzyme that will cleave the product at a recognition site, rendered double-stranded by an oligonucleotide complementary to the RCA product. Intact restriction oligonucleotides will displace the digested ones, e.g. during or after heat inactivation of the restriction enzyme. When an intact restriction hybridizes to one end of a monomerized RCA product, the other end of the monomer will hybridize to the same restriction oligonucleotide, because of the intra-molecular nature of the second hybridization reaction. The monomers can then be circularized by joining the ends, e.g. using a DNA ligase. The procedure can now be repeated for one or more rounds of the same procedure.

FIG. 10 shows real-time monitoring of the third-generation RCA described in example 1. A) Real-time measurement of HEX fluorescence emitted from molecular beacons hybridizing to the RCA product as it is generated. B) A graph showing the relationship between the amounts of target oligonucleotide added in the first probe circularization reaction, performed in quadruplicate, and the maximum slope of the third-generation real-time RCA of these ligation reactions. The error-bars denote the standard deviation.

FIG. 11 shows the fluorescence recorded at a microarray feature containing an oligonucleotide complementary to the second-generation RCA product obtained according to example 2.

Example 3

Oligonucleotides: The padlock probes used were p90: P-CCTCCCATCATATTAAAGGCTTTCTC-TATGTTAAGTGACCTACGACGATG CTGCTGCTG-TACTACTCTTCCTAAGGCATTCTGCAAACAT; SEQ ID NO:7 and p93: P-CCTCCCATCATATTAAAGGCTTTCTC-TATGTTAAGTGACCTAC GACCTCAATGCTGCTGCT-GTACTACTCTTCCTAAGGCATTCTGCA AACAT; SEQ ID NO:8 (P=5' phosphate). The ligation template for the padlock probes was t40: GCCTTTAATATGGGAGGAT-GTTTGCAGAGA ATGCCTTAG; SEQ ID NO:9. The DNA molecular beacon was FAM-cgcctcAATGCTGCTGCTG-TACTACgaggcg-DABCYL; SEQ ID NO:10 (the stem part in lower case) and the 2' O-Me-RNA molecular beacon was HEX-ccucAAUGCUGCUGCUGUACUACgagg-DAB-CYL; SEQ ID NO:11. The stem is two base pairs shorter in the 2'-O-Me-RNA beacon because of the higher hybrid stability of 2'-O-Me-RNA base pairs. The oligonucleotide used for restriction digestion was Tsp45I: GGCTTTCTCTATGT-TAAGTGACCTACGA; SEQ ID NO:12.

Example 4

Padlock probe circularization: 200 nM padlock probes were ligated in 10 mM Tris-acetate pH 7.5, 10 mM MgAcetate, 50 mM NaCl, 1 mM ATP, 1 µg/µl BSA, and 0.2 units/µl T4 DNA ligase (Amersham Pharmacia Biotech) at 37° C. for 30 minutes in presence of 600 nM ligation template.

Example 5

Rolling-circle amplification: Polymerization reactions were performed in 50 mM Tris-HCl (pH 7.5), 10 mM $MgCl_2$, 20 mM $(NH_4)_2SO_4$, 10 mM dithiothreitol and 0.2 µg/µl BSA, 0.25 mM dNTP, and 2 ng/µl Φ29 DNA polymerase (kindly provided by Dr. M. Salas) at 37° C. For real-time monitoring the RCA was performed in presence of 100 nM molecular beacon and 300 nM ROX dye. Fluorescence values are given as a ratio between the fluorescence emitted by the molecular beacon (FAM or HEX) and the ROX reference dye. The temperature profiles were obtained by sampling fluorescence after temperature increments of 1° C. held for 30 seconds.

Example 6

Restriction digestion: 20 µl of a 10 mM Bis Tris Propane-HCl (pH 7.0), 10 mM $MgCl_2$, 1 mM dithiothreitol, 0.1 µg/µl BSA, 1.5 µM Tsp45I, and 0.1 U/µl Tsp 45I (New England Biolabs) was added to 40 µl RCA products and incubated at 65° C. for four hours.

Figure 6:
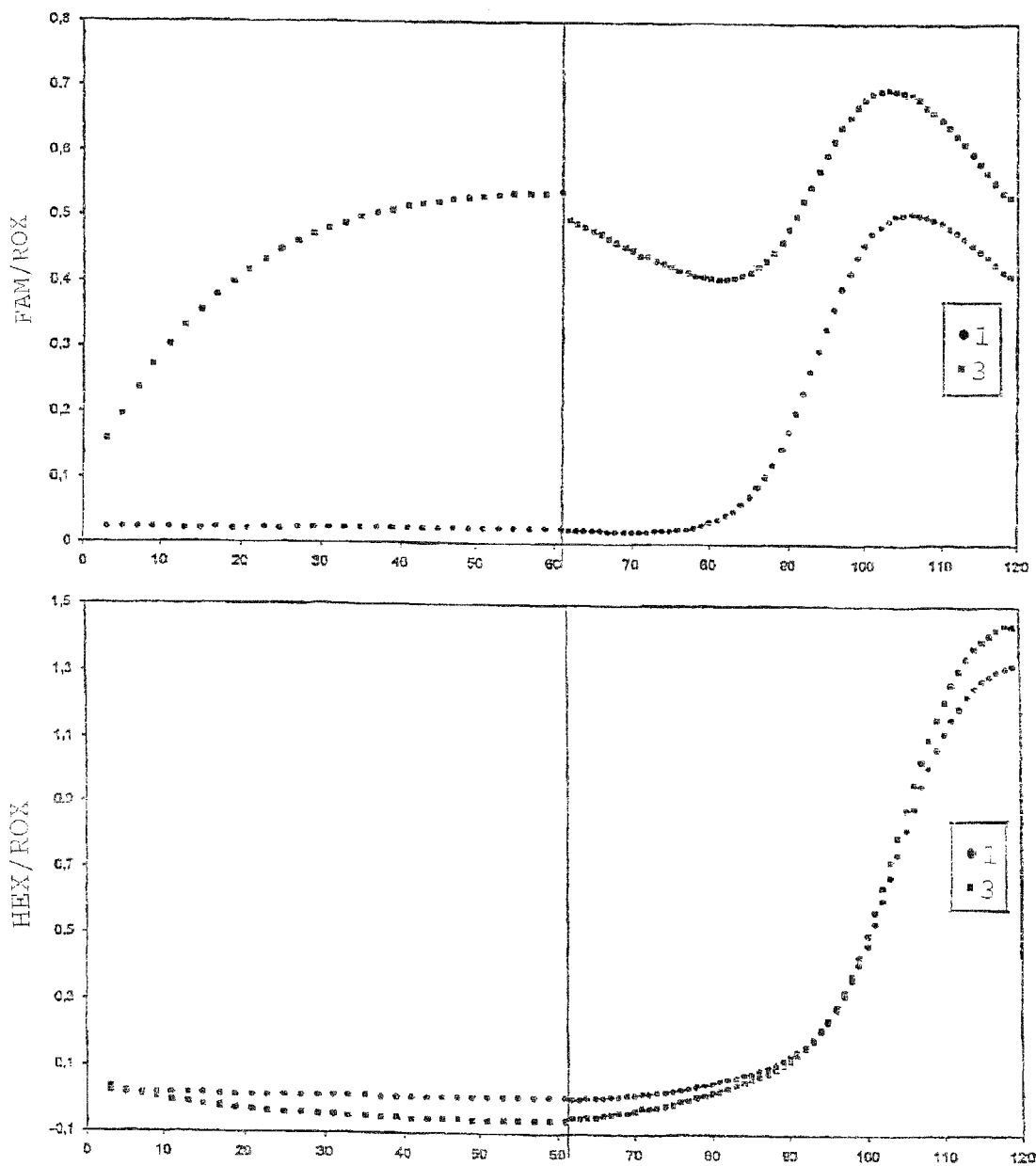

Turning to the drawings as can be seen in FIG. 6, removal of non-specific accumulation of fluorescence in presence of DNA polymerase by replacing all DNA residues of the molecular beacon with 2'-O-Me-RNA residues. One DNA molecular beacon labeled with FAM fluorescence (upper panel) and one 2'O-Me-RNA molecular beacon labeled with HEX fluorophore (lower panel) was added to the same test tube in presence (squares) or in absence (circles) of Φ29 DNA polymerase. The left portion of the graphs shows a real time monitoring of fluorescence in the test tube, and the right portion shows the temperature profile of the components present at the end of the 60 min incubation.

Figure 7:
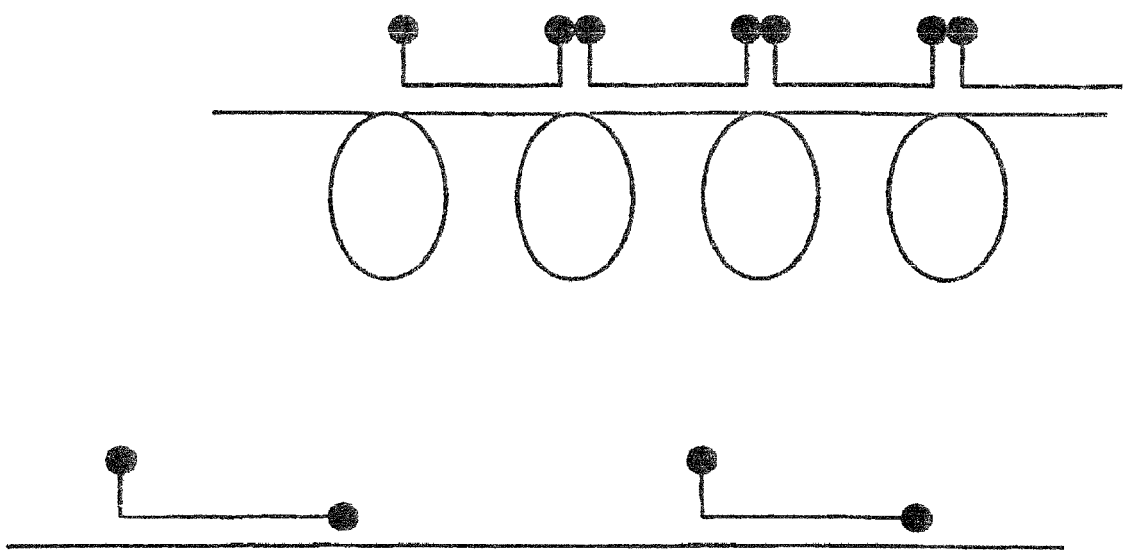
FIG. 7 is a schematic representation of inter-molecular quenching of molecular beacons hybridizing to an RCA product when using a traditional molecular beacon design.

From FIG. 7 it can be seen that inter-molecular quenching of molecular beacons hybridizing to an RCA product when using a traditional molecular beacon design (upper panel). The structure can be avoided by using a modified design (lower panel).

Figure 8:
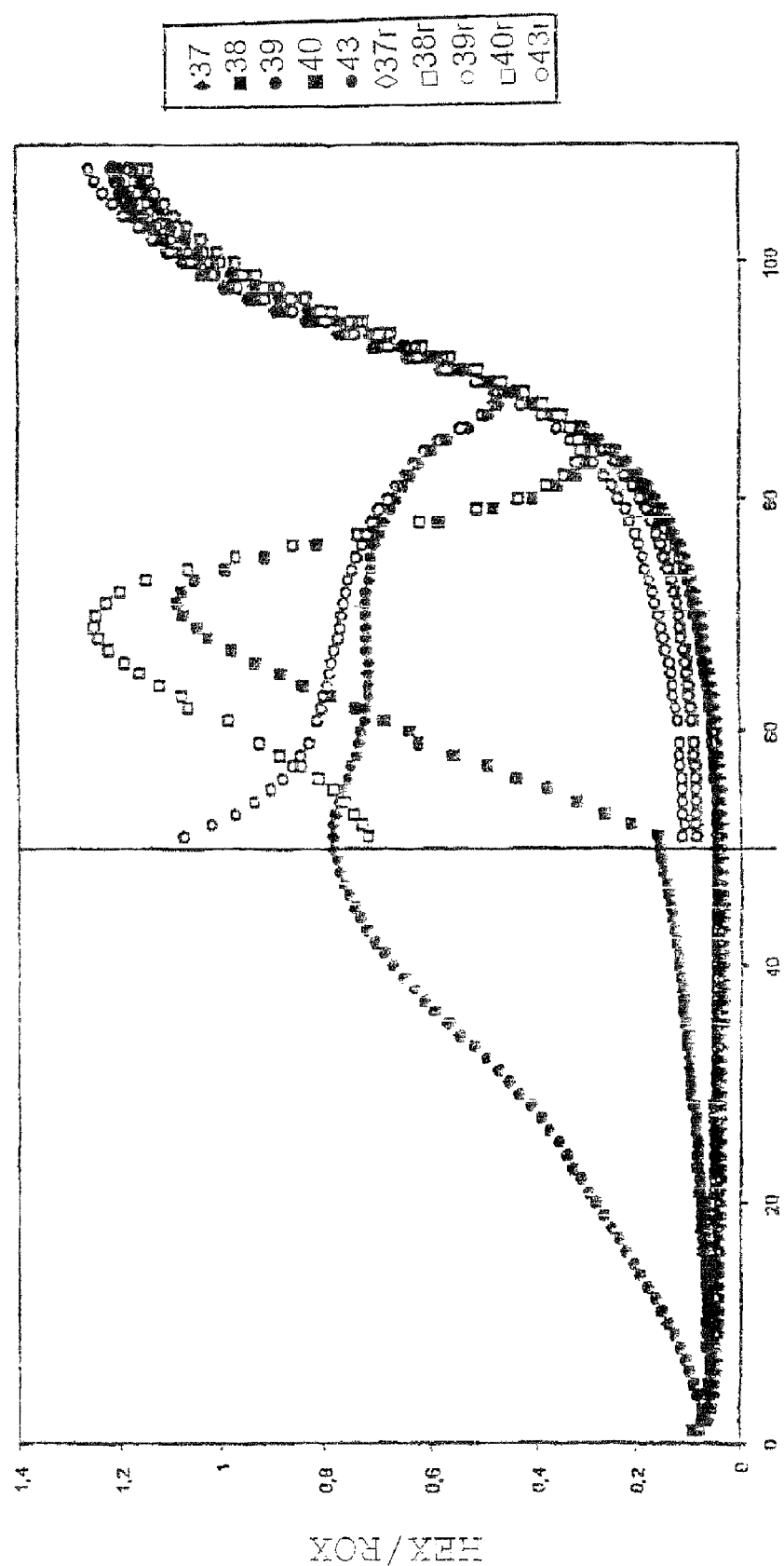
FIG. 8 is a graph showing the inter-molecular beacon quenching is demonstrated by restriction cleavage of the RCA product, and the modified design of the molecular beacon allows for real-time monitoring of RCA.

FIG. 8: The inter-molecular beacon quenching shown in FIG. 7 is demonstrated by restriction cleavage of the RCA product, and the modified design of the molecular beacon allows for real-time monitoring of RCA. RCA was performed on ligation reactions subjected to ligase (black) or no ligase (grey) containing either the p90 (squares) or the p93 (circles) padlock probes. The left portion of the graph shows a real time monitoring of fluorescence from the 2' O-Me-RNA molecular beacon in the different reactions. The right portion shows the temperature profile of the components present at the end of the 90 min RCA (filled symbols). Superimposed are the temperature profiles of the different reaction components after a restriction digest (open symbols).

Figure 9:
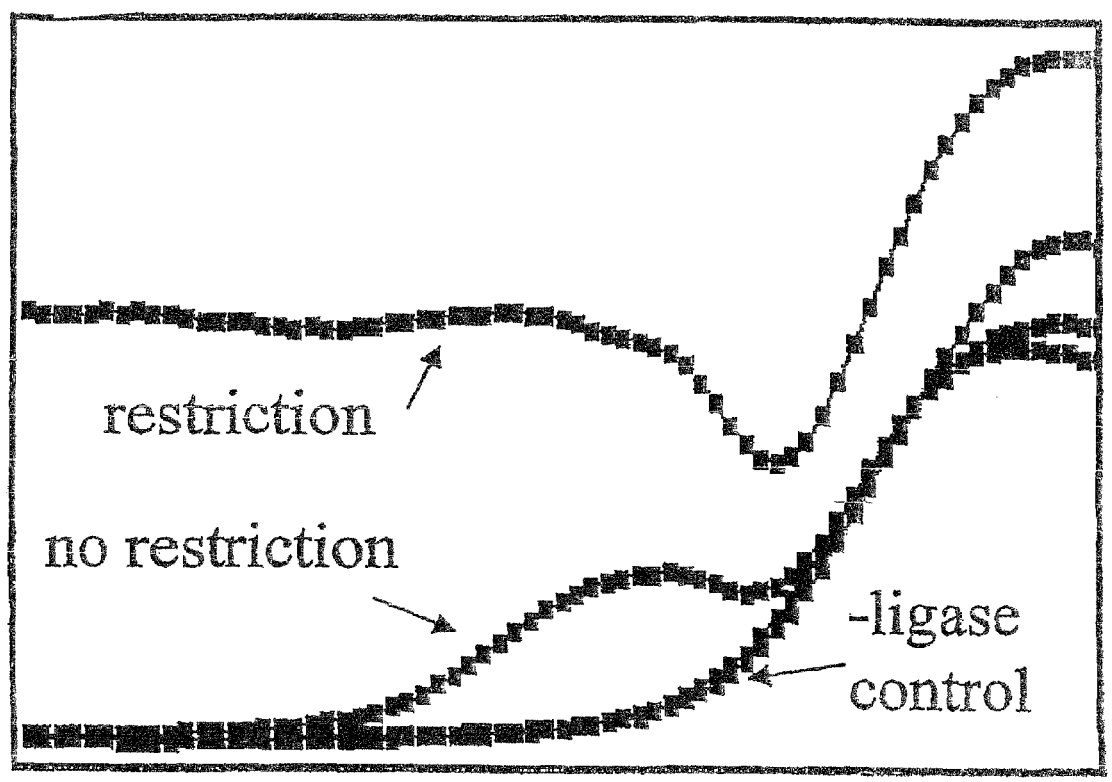
FIG. 9 is a graph showing the temperature profile of RCA reactions performed as in FIG. 8. Fluorescence is obtained from the DNA molecular beacon added after RCA, and heat inactivation of the polymerase.

Temperature profile of RCA reactions performed as in FIG. 8 are shown in FIG. 9 where fluorescence is obtained from the DNA molecular beacon added after RCA, and heat inactivation of the polymerase.

Example 7

One hundred nanogram of PstI-cut genomic DNA was denatured at 95° C. for 12 minutes and cooled rapidly in a thermal cycler to 12° C. Pre-annealed oligonucleotides "CircEx15ATP7B"; TTG CTG GCT TTT GTC TCG TAT CGG AGC GTA CCT AGA TAG CGT GCA GTC CTC TTT MT TTG; SEQ ID NO:13 and "gDNAadapter1°"; 5'P-CGC TAT CTA GGT ACG CTC CGA TAC AT; SEQ ID NO:14 were added to a final concentration of 2 nM to the denatured cut genomic DNA. To one reaction ligase was added, and to another ligase was omitted. Ligation was allowed to proceed for 1 h at room temperature followed by 30 minutes at 37° C. before the ligase was heat inactivated at 65° C. for 20 minutes. Five microliter of the ligase reaction were subjected to a rolling circle amplification reaction in 50 mM Tris-HCl, pH 7.5, mM $MgCl_2$, 20 mM $(NH_4)_2SO_4$, 0.2 µg/µl BSA, 0.25 mM dNTP, and 10 ng φ29 polymerase at 37° C. for 3 hours. To quantify the amount of RCA product, a real-time PCR reaction was run on 2.5 µl of the RCA reactions in 1×PCR GOLD buffer (ABI), 1.6 mM $MgCl_2$, 0.25 mM dNTP, 200 nM Ex15ATP7B-Frw (AGA CCT TGG GAT ACT GCA CGG; SEQ ID NO:15) and 200 nM Ex15ATP7B-Rew (CAA TTC CAC AGC CTG GCA CT; SEQ ID NO:16) primers, 0.625 U Taq GOLD polymerase (ABI), 300 nM ROX dye and 0.15× SYBR Green (Molecular Probes) in a volume of 25 µl. The primers were designed to PCR amplify both the genomic fragment and the RCA product. The PCR program was 95° C. for 10 minutes followed by 45 cycles of 95° C. for 15 sec and 60° C. for 60 sec. The PCR amplicons were subjected to a dissociation-curve analysis after the completion of the PCR. The results presented as Ct-values are shown in table 1 with standard deviations in brackets. The melting temperature of all amplicons was 82.6° C. which correlates well with the estimated Tm of 83° C. for the amplicon. φ29 DNA polymerase exhibits a strong exonucleolytic activity on single stranded DNA (denatured); therefore the non-ligated DNA shows 4-fold fewer products compared to the non-φ29 DNA polymerase treated sample when taking the four-fold dilution into account. The DNA to be amplified is 545 nt long and with a processivity of 1500 nt/min, a 500-fold amplification should be expected. This would be expected to result in a 120-fold amplification compared to the unamplified sample, when taking the four-fold dilution into account. The delta Ct-value of 6.75 corresponds to a 110-fold amplification.

TABLE 1

| SAMPLE | BEFORE RCA | AFTER RCA |
| --- | --- | --- |
| NO LIGASE | 25.27 (±0.191) | 29.06 (±0.255) |
| LIGASE | 25.98 (±0.057) | 19.23 (±0.212) |

Example 8

A 1×PBS solution of 2 pM RCA product from circularized padlock probes p93, and 5 nM of the product complementary rhodamine labeled probe RC1R (5'-Rhodamine-CTCTAT-GTTAAGTG ACCTACG; SEQ ID NO:17) was injected into two microfluidic channels with a width of 50 micrometer and a inter-channel spacing of 40 micrometer. Circularization of the padlock probe and the RCA was performed according to examples 4 and 5. The RCA products consist of on average 1500 copies of the circularized probes, since the RCA was performed for 1 hour. The fluorescence from bound and non-bound fluorescence labeled probes in the channels was imaged using an epifluorescence microscope equipped with a 40× dry lens. In FIG. 12, several bright balls of DNA are seen in the channels, as well as many less bright out-of-focus objects, on a background of the diffuse fluorescence from non-bound probes.

The invention is not limited to the embodiments hereinbefore described which may be varied in both construction and detail without departing from the spirit of the invention.

REFERENCES

Banér J., Nilsson M., Mendel-Hartvig M., and Landegren U. (1998). Signal amplification of padlock probes by rolling circle replication. *Nucleic Acids Res.* 22: 5073-5078.

Carmi N., Balkhi S. R., and Breaker R. R. (1998). Cleaving DNA with DNA. *Proc Natl Acad Sci USA* 95: 2233-7.

Copley C. G., and Boot C. (1992). Exonuclease cycling assay: an amplified assay for the detection of specific DNA sequences. *Biotechniques* 13: 888-92.

Cuenoud B., and Szostak J. W. (1995). A DNA metalloenzyme with DNA ligase activity. *Nature* 375: 611-4.

Daubendiek, S. L. and Kool, E. T. (1997) Generation of catalytic RNAs by rolling transcription of synthetic DNA nanocircles. *Nat Biotechnol,* 15: 273-277.

Dauwerse, J. G., Wiegant, J., Raap, A. K., Breuning, M. H. and van Ommen, G.-J. B. (1992) Multiple colors by fluorescence in situ hybridization using ratio-labelled DNA probes create a molecular karyotype. *Hum Mol Genet,* 1: 593-598.

Herschlag D., and Cech T. R. (1990). DNA cleavage catalysed by the ribozyme from Tetrahymena. *Nature* 344: 405-9.

Heid C. A., Stevens J., Livak K. J., and Williams P. M. (1996) Real time quantitative PCR. *Genome Research* 6: 986-994.

Lizardi P. M., Huang X., Zhu Z., Bray-Ward P., Thomas D. C., and Ward D. C. (1998). Mutation detection and single-molecule counting using isothermal rolling-circle amplification. *Nature Genet.* 19: 225-232.

Lyamichev V., Mast A. L., Hall J. G., Prudent J. R., Kaiser M. W., Takova T., Kwiatkowski R. W., Sander T. J., de Arruda M., Arco D. A., Neri B. P., and Brow M. A. D. (1999). Polymorphism identification and quantitative detection of genomic DNA by invasive cleavage of oligonucleotide probes. *Nat. Biotechnol.* 17: 292-296.

Nederlof, P. M., van, d. F. S., Vrolijk, J., Tanke, H. J. and Raap, A. K. (1992) Fluorescence ratio measurements of double-labeled probes for multiple in situ hybridization by digital imaging microscopy. *Cytometry,* 13: 839-845.

Nilsson, M., Malmgren, H., Samiotaki, M., Kwiatkowski, M., Chowdhary, B. P. and Landegren, U. (1994) Padlock probes: Circularizing oligonucleotides for localized DNA detection. *Science,* 265: 2085-2088.

Tyagi S., and Kramer F. R. (1996). Molecular beacons: probes that fluoresce upon hybridization. *Nat. Biotechnol.* 14: 303-308.

---

What is claimed is:

1. A method of generating circularized nucleic acid, said method comprising:
   providing a single-stranded target nucleic acid;
   hybridizing the single-stranded target nucleic acid with a circularization adaptor having
   (i) single-stranded sequences at each end and on the same strand, which single-stranded sequences are complementary to the ends of the single-stranded target nucleic acid and
   (ii) a double-stranded non-target complementary segment between said single-stranded end sequences; and
   circularizing the target nucleic acid using a DNA ligase.

2. The method of claim 1, wherein said circularization adaptor contains a restriction oligonucleotide sequence in said double-stranded segment.

3. The method of claim 1, further comprising amplifying said circularized nucleic acid.

4. The method of claim 3, wherein said amplification is rolling circle amplification.

5. The method of claim 1, wherein said single-stranded target nucleic acid is obtained by fragmenting a double-stranded nucleic acid using one or more restriction enzymes or FLAP endonucleases and then denaturing the resulting fragments.

6. The method of claim 1, wherein a multiplicity of different nucleic acid fragments are circularized in parallel using different circularization adaptors.

7. The method of claim 6, wherein the different circularization adaptors contain the same restriction oligonucleotide sequence and wherein a multiplicity of different nucleic acid fragments are amplified in parallel.

8. The method of claim 1, wherein the circularized nucleic acid comprises cDNA or genomic DNA.

9. A method of amplifying a target nucleic acid fragment, said method comprising:
   (i) fragmenting a target nucleic acid,
   (ii) circularizing a target nucleic acid fragment thus obtained, using a circularization adaptor having single-stranded sequences at each end complementary to the ends of the target fragment and, between said single-stranded end sequences, a double-stranded non-target-complementary segment, and
   (iii) amplifying said circularized target nucleic acid fragment.

10. A method of analyzing at least one circularized nucleic acid, the method comprising amplifying the said circularized nucleic acid to provide an amplification product free in solution which comprises a concatemer of a sequence to be analysed coiled into a ball, the method further comprising the step of:
   directly detecting by microscopic analysis said concatemer amplification product ball which is free in solution in a homogeneous detection reaction by hybridizing hybridization probes being fluorescence-labelled oligonucleotides to said amplification product ball, wherein the hybridization of the oligonucleotides results in an enrichment of the oligonucleotides in said amplification product ball and said enrichment causes a condensed signal which can be directly detected by microscopic analysis due to the contrast between said condensed signal and the diffuse signal from non-bound oligonucleotides.

11. The method of claim 10, wherein the signalling probes are singly or ratio-labelled.

12. The method claim 10, wherein the circularized nucleic acid to be analysed is a probe sequence.

13. The method of claim 10, wherein the circularized nucleic acid to be analysed comprises cDNA, genomic DNA or RNA sequences.

14. The method of claim 10, wherein the circularized nucleic acid to be analysed is circularized using cDNA, genomic DNA, or RNA sequence.

15. The method of claim 10, wherein said circularized nucleic acid is formed by hybridizing to a linear nucleic acid an oligonucleotide complementary to both end sequences of said linear nucleic acid and ligating said end sequences.

16. A method for generating a circularized nucleic acid molecule from two oligonucleotides, being parts of a pair of proximity probes, that have been joined in a proximity-dependent nucleic acid ligation reaction to form a joined product, said method comprising:
   hybridizing a restriction oligonucleotide to two identical sequences present in both of the joined oligonucleotides in said joined product, digesting said joined product at the restriction sites thus created to release a linear nucleic acid molecule, and circularizing said released linear nucleic acid molecule by ligation by using an intact restriction oligonucleotide as a ligation template, said intact restriction oligonucleotide being complementary to both ends of said released linear molecule.

17. The method of claim 16, further comprising amplifying said circularized nucleic acid molecule.

18. The method of claim 17, wherein said amplification is rolling circle amplification.

19. The method of claim 16, wherein said restriction oligonucleotide is present in excess.

20. The method of claim 16, further comprising, after the digesting step, a heating step that inactivates the restriction enzyme and denatures the joined product.

21. The method claim 16, wherein the ligatable ends of the oligonucleotides that have been joined to form a joined product constitute unique half-tag sequences.

22. The method of claim 16, wherein the oligonucleotides that have been joined to form a joined product are joined by blunt-end ligation.

* * * * *

SEQUENCE LISTING

```
<160> NUMBER OF SEQ ID NOS: 17

<210> SEQ ID NO 1
<211> LENGTH: 93
<212> TYPE: DNA
<213> ORGANISM: Artificial
<220> FEATURE:
<223> OTHER INFORMATION: Synthetic

<400> SEQUENCE: 1
cctcccatca tattaaaggc tttctctatg ttaagtgacc tacgacctca atgctgctgc      60
tgtactactc ttcctaaggc attctgcaaa cat                                  93

<210> SEQ ID NO 2
<211> LENGTH: 37
<212> TYPE: DNA
<213> ORGANISM: Artificial
<220> FEATURE:
<223> OTHER INFORMATION: Synthetic

<400> SEQUENCE: 2
gcctttaata tgggaggatg tttgcagaat gccttag                              37

<210> SEQ ID NO 3
<211> LENGTH: 20
<212> TYPE: DNA
<213> ORGANISM: Artificial
<220> FEATURE:
<223> OTHER INFORMATION: Synthetic

<400> SEQUENCE: 3
cgtcgtaggt cacttaacat                                                 20

<210> SEQ ID NO 4
<211> LENGTH: 19
<212> TYPE: DNA
<213> ORGANISM: Artificial
<220> FEATURE:
<223> OTHER INFORMATION: Synthetic
```

```
<400> SEQUENCE: 4
gctgctgtac tactctctt                                              19

<210> SEQ ID NO 5
<211> LENGTH: 19
<212> TYPE: DNA
<213> ORGANISM: Artificial
<220> FEATURE:
<223> OTHER INFORMATION: Synthetic

<400> SEQUENCE: 5
aagagagtag tacagcagc                                              19

<210> SEQ ID NO 6
<211> LENGTH: 27
<212> TYPE: RNA
<213> ORGANISM: Artificial
<220> FEATURE:
<223> OTHER INFORMATION: Synthetic

<400> SEQUENCE: 6
ccucaaugcu gcugcuguac uacgagg                                     27

<210> SEQ ID NO 7
<211> LENGTH: 90
<212> TYPE: DNA
<213> ORGANISM: Artificial
<220> FEATURE:
<223> OTHER INFORMATION: Synthetic

<400> SEQUENCE: 7
cctcccatca tattaaaggc tttctctatg ttaagtgacc tacgacgatg ctgctgctgt  60
actactcttc ctaaggcatt ctgcaaacat                                  90

<210> SEQ ID NO 8
<211> LENGTH: 93
<212> TYPE: DNA
<213> ORGANISM: Artificial
<220> FEATURE:
<223> OTHER INFORMATION: Synthetic

<400> SEQUENCE: 8
cctcccatca tattaaaggc tttctctatg ttaagtgacc tacgacctca atgctgctgc  60
tgtactactc ttcctaaggc attctgcaaa cat                              93

<210> SEQ ID NO 9
<211> LENGTH: 37
<212> TYPE: DNA
<213> ORGANISM: Artificial
<220> FEATURE:
<223> OTHER INFORMATION: Synthetic

<400> SEQUENCE: 9
gcctttaata tgggaggatg tttgcagaat gccttag                          37

<210> SEQ ID NO 10
<211> LENGTH: 31
<212> TYPE: DNA
<213> ORGANISM: Artificial
<220> FEATURE:
<223> OTHER INFORMATION: Synthetic

<400> SEQUENCE: 10
```
cgcctcaatg ctgctgctgt actacgaggc g            31

<210> SEQ ID NO 11
<211> LENGTH: 27
<212> TYPE: RNA
<213> ORGANISM: Artificial
<220> FEATURE:
<223> OTHER INFORMATION: Synthetic

<400> SEQUENCE: 11
ccucaaugcu gcugcuguac uacgagg                 27

<210> SEQ ID NO 12
<211> LENGTH: 28
<212> TYPE: DNA
<213> ORGANISM: Artificial
<220> FEATURE:
<223> OTHER INFORMATION: Synthetic

<400> SEQUENCE: 12
ggctttctct atgttaagtg acctacga                28

<210> SEQ ID NO 13
<211> LENGTH: 60
<212> TYPE: DNA
<213> ORGANISM: Artificial
<220> FEATURE:
<223> OTHER INFORMATION: Synthetic

<400> SEQUENCE: 13
ttgctggctt ttgtctcgta tcggagcgta cctagatagc gtgcagtcct ctttaatttg    60

<210> SEQ ID NO 14
<211> LENGTH: 26
<212> TYPE: DNA
<213> ORGANISM: Artificial
<220> FEATURE:
<223> OTHER INFORMATION: Synthetic

<400> SEQUENCE: 14
cgctatctag gtacgctccg atacat                  26

<210> SEQ ID NO 15
<211> LENGTH: 21
<212> TYPE: DNA
<213> ORGANISM: Artificial
<220> FEATURE:
<223> OTHER INFORMATION: Synthetic

<400> SEQUENCE: 15
agaccttggg atactgcacg g                       21

<210> SEQ ID NO 16
<211> LENGTH: 20
<212> TYPE: DNA
<213> ORGANISM: Artificial
<220> FEATURE:
<223> OTHER INFORMATION: Synthetic

<400> SEQUENCE: 16
caattccaca gcctggcact                         20

<210> SEQ ID NO 17
<211> LENGTH: 21
<212> TYPE: DNA
<213> ORGANISM: Artificial

-continued

```
<220> FEATURE:
<223> OTHER INFORMATION: Synthetic

<400> SEQUENCE: 17
ctctatgtta agtgacctac g                                              21
```